United States Patent [19]
Wong et al.

[11] Patent Number: 5,693,658
[45] Date of Patent: Dec. 2, 1997

[54] IMIDAZOLINONES

[75] Inventors: Rosie Bick-Har Wong, Piscataway, N.J.; Joseph Luke Pont, Klein-Winternheim, Germany; Alvin Donald Crews, Jr., Voorhees, N.J.

[73] Assignee: American Cyanamid Company, Madison, N.J.

[21] Appl. No.: 333,826

[22] Filed: Nov. 3, 1994

[51] Int. Cl.$^6$ .................... C07D 401/04; A61K 31/44
[52] U.S. Cl. .................... 514/341; 546/274.1; 546/16; 548/325.5; 514/278; 514/386
[58] Field of Search .................... 546/278, 16, 274.1; 548/325.5; 514/341, 278, 386

[56] References Cited

U.S. PATENT DOCUMENTS

| | | | |
|---|---|---|---|
| 4,798,619 | 1/1989 | Los | 546/5 |
| 5,342,771 | 8/1994 | Wong et al. | 435/188 |

OTHER PUBLICATIONS

American Cyanamid Company allowed U.S. Patent Application, Serial No. 08/023,321 filed on Feb. 25, 1993.

*Primary Examiner*—Jane Fan
*Attorney, Agent, or Firm*—John W. Hogan, Jr.

[57] ABSTRACT

The present invention provides an imidazolinone hapten having the structural formula

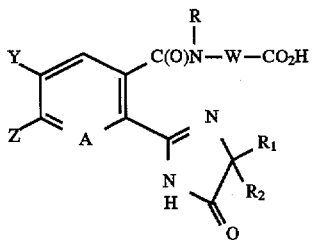
(I)

or

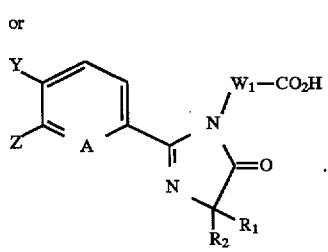
(II)

Further provided are an antigen and an enzyme conjugate which are prepared from the imidazolinone hapten. The haptens, antigens and enzyme conjugates provided are useful in immunoassays for determining the presence and concentration of an imidazolinone compound in the presence of one or more other imidazolinone compounds.

11 Claims, No Drawings

IMIDAZOLINONES

BACKGROUND OF THE INVENTION

The discovery, development and commercialization of the imidazolinone compounds has given new meaning to the term "weed control"; for within this series of compounds it has been found that some are broad-spectrum or total vegetation herbicides with activity in both herbaceous and woody plants while others are highly selective weed control agents useful in the presence of crops. The imidazolinones are best exemplified by the commercial compounds imazethapyr, imazaquin, imazamethabenz-methyl and imazapyr.

Imidazolinone compounds are used by farmers throughout the world to control undesirable plant species. In certain areas, several imidazolinone compounds are individually used to control weeds growing in the presence of different crops such as soybeans, corn, peanuts, wheat, barley, rye and sunflowers, among others.

Although imidazolinone compounds gradually degrade in the environment, residues remaining in the soil should be monitored so as to provide the most efficacious weed control while avoiding possible damage to follow crop plants. It is particularly important to monitor individual imidazolinone residues in those areas where several imidazolinones are used.

An enzyme-linked immunosorbent assay for the detection of imidazolinone compounds is described in allowed U.S. patent application Ser. No. 08/023,321, filed on Feb. 25, 1993. However, the polyclonal antibodies described in that patent application are not specific enough to determine the presence and concentration of an imidazolinone compound in the presence of one or more other imidazolinone compounds.

It is an object of the present invention to provide haptens and antigens and enzyme conjugates prepared therefrom which are useful in a method for determining the presence and concentration of an imidazolinone compound in the presence of one or more other imidazolinone compounds.

SUMMARY OF THE INVENTION

The present invention provides imidazolinone haptens and antigens and enzyme conjugates which are prepared from the imidazolinone haptens.

The antigens of the present invention are used to prepare imidazolinone specific monoclonal antibodies. Advantageously, certain of those monoclonal antibodies are used to determine the presence and concentration of an imidazolinone compound in the presence of one or more other imidazolinone compounds.

The enzyme conjugates of the present invention are used in a direct competition immunoassay to determine the presence and concentration of an imidazolinone compound.

DETAILED DESCRIPTION OF THE INVENTION

The present invention provides imidazolinone haptens that are used to prepare antigens which elicit imidazolinone specific antibody production in animals.

The imidazolinone haptens of the present invention have the structural formula

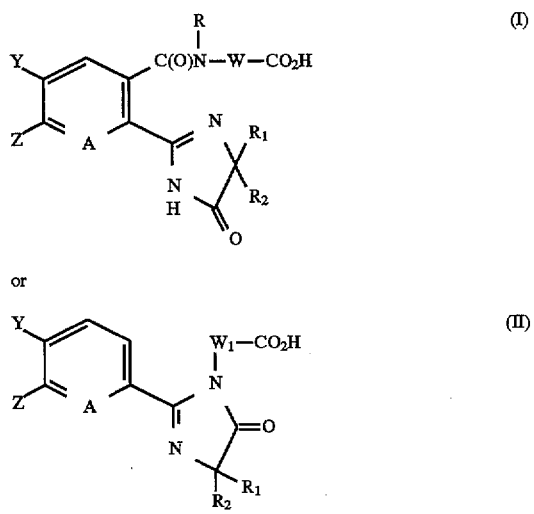

wherein

R is hydrogen or $C_1$–$C_4$alkyl;

$R_1$ is $C_1$–$C_4$alkyl;

$R_2$ is $C_1$–$C_4$alkyl or $C_3$–$C_6$cycloalkyl; and when $R_1$ and $R_2$ are taken together with the carbon atom to which they are attached they may represent $C_3$–$C_6$cycloalkyl optionally substituted with methyl;

Y and Z are each independently hydrogen, halogen, $C_1$–$C_6$alkyl, $C_1$–$C_4$alkoxyalkyl, $C_1$–$C_4$hydroxyalkyl, $C_1$–$C_4$alkoxy, $C_1$–$C_4$alkylthio, phenoxy, $C_1$–$C_4$haloalkyl, nitro, cyano, $C_1$–$C_4$alkylamino, di($C_1$–$C_4$alkyl)amino, $C_1$–$C_4$alkylsulfonyl or phenyl optionally substituted with one $C_1$–$C_4$alkyl group, $C_1$–$C_4$alkoxy group or halogen atom; and when taken together, Y and Z may form a ring in which YZ are represented by the structure: —$(CH_2)_n$—, where n is an integer of 3 or 4; or

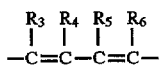

where $R_3$, $R_4$, $R_5$ and $R_6$ are each independently hydrogen, halogen, $C_1$–$C_4$alkyl or $C_1$–$C_4$alkoxy;

A is N or CH;

W is $C_3$–$C_{12}$alkylene optionally substituted with one or two $C_1$–$C_3$alkyl groups, $C_1$–$C_3$alkoxy groups, oxo groups or halogen atoms, and optionally interrupted by one oxygen or sulfur atom, $C_3$–$C_{12}$alkenylene optionally substituted with one or two $C_1$–$C_3$alkyl groups, $C_1$–$C_3$alkoxy groups, oxo groups or halogen atoms, and optionally interrupted by one oxygen or sulfur atom, or $C_3$–$C_{12}$alkynylene optionally substituted with one or two $C_1$–$C_3$alkyl groups, $C_1$–$C_3$alkoxy groups, oxo groups or halogen atoms, and optionally interrupted by one oxygen or sulfur atom; and $W_1$ is $C_1$–$C_{12}$alkylene optionally substituted with one or two $C_1$–$C_3$alkyl groups, $C_1$–$C_3$alkoxy groups, oxo groups or halogen atoms, and optionally interrupted by one oxygen or sulfur atom, $C_2$–$C_{12}$alkenylene optionally substituted with one or two $C_1$–$C_3$alkyl groups, $C_1$–$C_3$alkoxy groups, oxo groups or halogen atoms, and optionally interrupted by one oxygen or sulfur atom, or $C_3$–$C_{12}$alkynylene optionally substituted with one or two $C_1$–$C_3$alkyl groups, $C_1$–$C_3$alkoxy groups, oxo groups or halogen atoms, and optionally interrupted by one oxygen or sulfur atom.

Preferred formula I and II haptens are those wherein

R is hydrogen or methyl;

$R_1$ is methyl;

$R_2$ is isopropyl;

Y is hydrogen, $C_1$–$C_4$alkyl or $C_1$–$C_4$alkoxyalkyl;

Z is hydrogen; and when taken together, Y and Z may form a ring in which YZ is represented by the structure: —CH=CH—CH=CH—;

A is N or CH;

W is $C_3$–$C_{12}$alkylene or $C_3$–$C_{12}$alkenylene; and $W_1$ is $C_1$–$C_{12}$alkylene or $C_2$–$C_{12}$alkenylene.

More preferred formula I and II haptens which are used to prepare antigens which elicit imidazolinone specific antibody production in animals are those wherein R is hydrogen or methyl;

$R_1$ is methyl;

$R_2$ is isopropyl;

Y is hydrogen, methyl, ethyl or methoxymethyl;

Z is hydrogen; and when taken together, Y and Z may form a ring in which YZ is represented by the structure: —CH=CH—CH=CH—;

A is N;

W is $C_3$–$C_6$alkylene or $C_3$–$C_6$alkenylene; and $W_1$ is $C_1$–$C_6$alkylene or $C_2$–$C_6$alkenylene.

Imidazolinone haptens of the present invention which are particularly useful in the preparation of antigens include 6-[5-ethyl-2-(4-isopropyl-4-methyl-5-oxo-2-imidazolin-2-yl)nicotinamido]hexanoic acid;

2-(5-ethyl-2-pyridyl)-4-isopropyl-4-methyl-5-oxo-2-imidazoline-1-valeric acid;

4-[5-ethyl-2-(4-isopropyl-4-methyl-5-oxo-2-imidazolin-2-yl)nicotinamido]butyric acid;

2-(5-ethyl-2-pyridyl)-4-isopropyl-4-methyl-5-oxo-2-imidazoline-1-crotonic acid, (E)-;

2-(5-ethyl-2-pyridyl)-4-isopropyl-4-methyl-5-oxo-2-imidazoline- 1-acetic acid; and 4-[5-ethyl-2-(4-isopropyl-4-methyl-5-oxo-2-imidazolin-2-yl)-N-methylnicotinoamido]butyric acid, among others.

The antigens of the present invention which are prepared from the imidazolinone haptens described above and are useful in the production of imidazolinone specific antibodies in animals have the structural formula

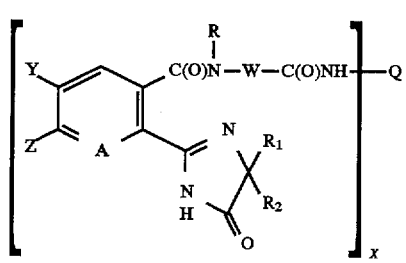 (III)

or

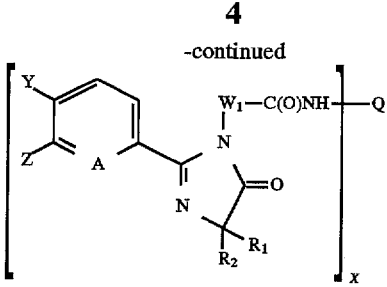 (IV)

wherein

R is hydrogen or $C_1$–$C_4$alkyl;

$R_1$ is $C_1$–$C_4$alkyl;

$R_2$ is $C_1$–$C_4$alkyl or $C_3$–$C_6$cycloalkyl; and when $R_1$ and $R_2$ are taken together with the carbon atom to which they are attached they may represent $C_3$–$C_6$cycloalkyl optionally substituted with methyl;

Y and Z are each independently hydrogen, halogen, $C_1$–$C_6$alkyl, $C_1$–$C_4$alkoxyalkyl, $C_1$–$C_4$hydroxyalkyl, $C_1$–$C_4$alkoxy, $C_1$–$C_4$alkylthio, phenoxy, $C_1$–$C_4$haloalkyl, nitro, cyano, $C_1$–$C_4$alkylamino, di($C_1$–$C_4$alkyl)amino, $C_1$–$C_4$alkylsulfonyl or phenyl optionally substituted with one $C_1$–$C_4$alkyl group, $C_1$–$C_4$alkoxy group or halogen atom; and when taken together, Y and Z may form a ring in which YZ are represented by the structure: —($CH_2$)$_n$—, where n is an integer of 3 or 4; or

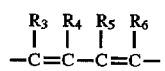

where $R_3$, $R_4$, $R_5$ and $R_6$ are each independently hydrogen, halogen, $C_1$–$C_4$alkyl or $C_1$–$C_4$alkoxy;

A is N or CH;

W is $C_3$–$C_{12}$alkylene optionally substituted with one or two $C_1$–$C_3$alkyl groups, $C_1$–$C_3$alkoxy groups, oxo groups or halogen atoms, and optionally interrupted by one oxygen or sulfur atom, $C_3$–$C_{12}$alkenylene optionally substituted with one or two $C_1$–$C_3$alkyl groups, $C_1$–$C_3$alkoxy groups, oxo groups or halogen atoms, and optionally interrupted by one oxygen or sulfur atom, or $C_3$–$C_{12}$alkynylene optionally substituted with one or two $C_1$–$C_3$alkyl groups, $C_1$–$C_3$alkoxy groups, oxo groups or halogen atoms, and optionally interrupted by one oxygen or sulfur atom;

$W_1$ is $C_1$–$C_{12}$alkylene optionally substituted with one or two $C_1$–$C_3$alkyl groups, $C_1$–$C_3$alkoxy groups, oxo groups or halogen atoms, and optionally interrupted by one oxygen or sulfur atom, $C_2$–$C_{12}$alkenylene optionally substituted with one or two $C_1$–$C_3$alkyl groups, $C_1$–$C_3$alkoxy groups, oxo groups or halogen atoms, and optionally interrupted by one oxygen or sulfur atom, or $C_3$–$C_{12}$alkynylene optionally substituted with one or two $C_1$–$C_3$alkyl groups, $C_1$–$C_3$alkoxy groups, oxo groups or halogen atoms, and optionally interrupted by one oxygen or sulfur atom;

X is an integer from about 1 to 40; and

Q is a protein.

Proteins suitable for use in the antigens of this invention include cationized bovine serum albumin, keyhole limpet hemocyanin, ovalbumin, bovine serum albumin, thyroglobulin, human serum albumin, fibrinogen and the like.

Preferred formula III and IV antigens of the present invention are those wherein R is hydrogen or methyl;

$R_1$ is methyl;

$R_2$ is isopropyl;

Y is hydrogen, $C_1$–$C_4$alkyl or $C_1$–$C_4$alkoxyalkyl;

Z is hydrogen; and when taken together, Y and Z may form a ring in which YZ is represented by the structure: —CH=CH—CH=CH—;

A is N or CH;

W is $C_3$–$C_{12}$alkylene or $C_3$–$C_{12}$alkenylene;

$W_1$ is $C_1$–$C_{12}$alkylene or $C_2$–$C_{12}$alkenylene;

X is an integer from about 1 to 40; and

Q is a protein.

More preferred formula III and IV antigens which elicit imidazolinone specific antibody production in animals are those wherein R is hydrogen or methyl;

$R_1$ is methyl;

$R_2$ is isopropyl;

Y is hydrogen, methyl, ethyl or methoxymethyl;

Z is hydrogen; and when taken together, Y and Z may form a ring in which YZ is represented by the structure: —CH=CH—CH=CH—;

A is N;

W is $C_3$–$C_6$alkylene or $C_3$–$C_6$alkenylene;

$W_1$ is $C_1$–$C_6$alkylene or $C_2$–$C_6$alkenylene;

X is an integer from about 1 to 40; and

Q is a protein.

Antigens of the present invention which are especially useful in the production of imidazolinone specific antibodies are those having the following structural formula

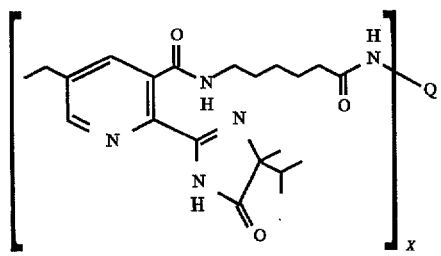
(V)

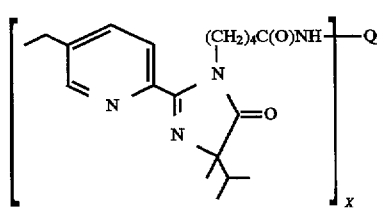
(VI)

or

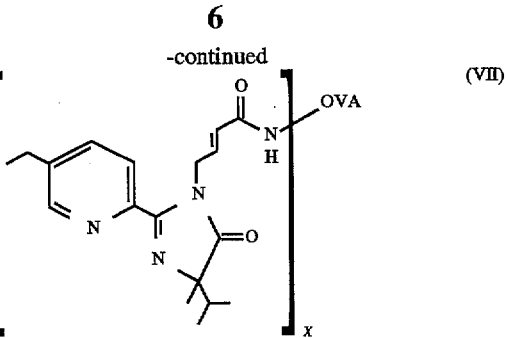
(VII)

wherein

X is an integer from about 1 to 40;

OVA is ovalbumin; and

Q is keyhole limpet hemocyanin or cationized bovine serum albumin.

The present invention further provides enzyme conjugates which are used in a direct competition immunoassay to determine the presence of imidazolinone compounds in water, soil or plant samples.

The enzyme conjugates of the present invention have the structural formula

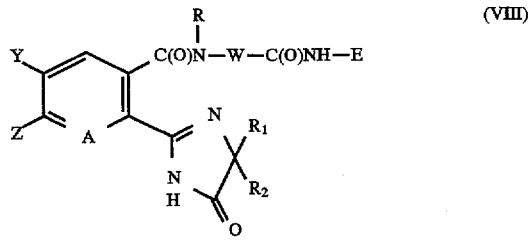
(VIII)

or

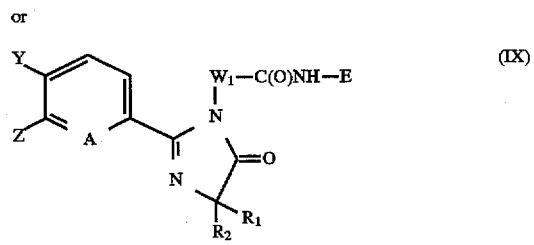
(IX)

wherein

R is hydrogen or $C_1$–$C_4$alkyl;

$R_1$ is $C_1$–$C_4$alkyl;

$R_2$ is $C_1$–$C_4$alkyl or $C_3$–$C_6$cycloalkyl; and when $R_1$ and $R_2$ are taken together with the carbon atom to which they are attached they may represent $C_3$–$C_6$cycloalkyl optionally substituted with methyl;

Y and Z are each independently hydrogen, halogen, $C_1$–$C_6$alkyl, $C_1$–$C_4$alkoxyalkyl, $C_1$–$C_4$hydroxyalkyl, $C_1$–$C_4$alkoxy, $C_1$–$C_4$alkylthio, phenoxy, $C_1$–$C_4$haloalkyl, nitro, cyano, $C_1$–$C_4$alkylamino, di($C_1$–$C_4$alkyl)amino, $C_1$–$C_4$alkylsulfonyl or phenyl optionally substituted with one $C_1$–$C_4$alkyl group, $C_1$–$C_4$alkoxy group or halogen atom; and when taken together, Y and Z may form a ring in which YZ are represented by the structure: —$(CH_2)_n$—, where n is an integer of 3 or 4; or

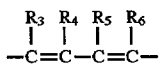

where $R_3$, $R_4$, $R_5$ and $R_6$ are each independently hydrogen, halogen, $C_1$–$C_4$alkyl or $C_1$–$C_4$alkoxy;

A is N or CH;

W is $C_3$-$C_{12}$alkylene optionally substituted with one or two $C_1$-$C_3$alkyl groups, $C_1$-$C_3$alkoxy groups, oxo groups or halogen atoms, and optionally interrupted by one oxygen or sulfur atom, $C_3$-$C_{12}$alkenylene optionally substituted with one or two $C_1$-$C_3$alkyl groups, $C_1$-$C_3$alkoxy groups, oxo groups or halogen atoms, and optionally interrupted by one oxygen or sulfur atom, or $C_3$-$C_{12}$alkynylene optionally substituted with one or two $C_1$-$C_3$alkyl groups, $C_1$-$C_3$alkoxy groups, oxo groups or halogen atoms, and optionally interrupted by one oxygen or sulfur atom;

$W_1$ is $C_1$-$C_{12}$alkylene optionally substituted with one or two $C_1$-$C_3$alkyl groups, $C_1$-$C_3$alkoxy groups, oxo groups or halogen atoms, and optionally interrupted by one oxygen or sulfur atom, $C_2$-$C_{12}$alkenylene optionally substituted with one or two $C_1$-$C_3$alkyl groups, $C_1$-$C_3$alkoxy groups, oxo groups or halogen atoms, and optionally interrupted by one oxygen or sulfur atom, or $C_3$-$C_{12}$alkynylene optionally substituted with one or two $C_1$-$C_3$alkyl groups, $C_1$-$C_3$alkoxy groups, oxo groups or halogen atoms, and optionally interrupted by one oxygen or sulfur atom; and E is an enzyme.

Enzymes suitable for use in the enzyme conjugates of the present invention include those that produce a color change when treated with a substrate. Preferred enzymes are alkaline phosphatase, horseradish peroxidase, urease, glucose oxidase and galactosidase.

Preferred formula VIII and IX enzyme conjugates are those wherein

R is hydrogen or methyl;

$R_1$ is methyl;

$R_2$ is isopropyl;

Y is hydrogen, $C_1$-$C_4$alkyl or $C_1$-$C_4$alkoxyalkyl;

Z is hydrogen; and when taken together, Y and Z may form a ring in which YZ is represented by the structure: —CH=CH—CH=CH—;

A is N or CH;

W is $C_3$-$C_{12}$alkylene or $C_3$-$C_{12}$alkenylene;

$W_1$ is $C_1$-$C_{12}$alkylene or $C_2$-$C_{12}$alkenylene; and

E is an enzyme.

More preferred formula VIII and IX enzyme conjugates of the present invention are those wherein R is hydrogen or methyl;

$R_1$ is methyl;

$R_2$ is isopropyl;

Y is hydrogen, methyl, ethyl or methoxymethyl;

Z is hydrogen; and when taken together, Y and Z may form a ring in which YZ is represented by the structure: —CH=CH—CH=CH—;

A is N;

W is $C_3$-$C_6$alkylene or $C_3$-$C_6$alkenylene;

$W_1$ is $C_1$-$C_6$alkylene or $C_2$-$C_6$alkenylene; and

E is an enzyme.

One of the most preferred enzyme conjugates of this invention has the following structural formula

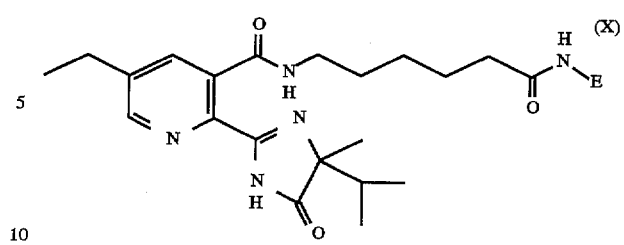

wherein

E is alkaline phosphatase.

The formula I haptens of the present invention may be prepared by reacting a compound having the structural formula XI

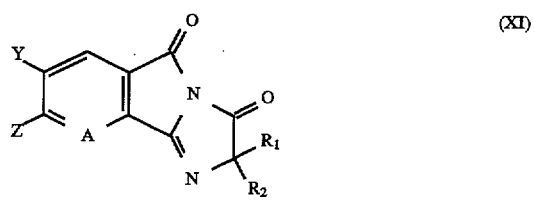

wherein Y, Z, A, $R_1$ and $R_2$ are as described hereinabove with an amino acid compound having the structural formula XII

wherein R and W are as described hereinabove; and the acid addition salts thereof in the presence of a trialkylamine such as triethylamine and a polar solvent such as N,N-dimethylformamide to form a reaction mixture which is quenched with aqueous acid to form the desired formula I hapten. The above reaction scheme is shown in Flow Diagram I.

FLOW DIAGRAM I

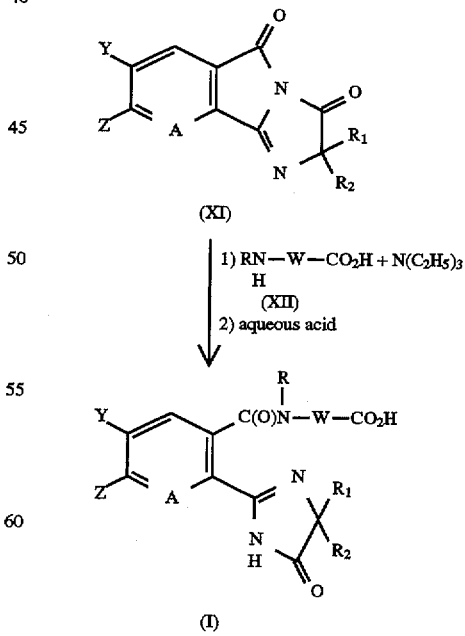

Alternatively, formula I haptens may be prepared by reacting a compound having the structural formula XI with an amino acid ester having the structural formula XIII

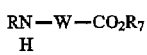   (XIII)

wherein

R and W are as described hereinabove;

$R_7$ is $C_1$–$C_4$alkyl; and the acid addition salts thereof in the presence of a trialkylamine such as triethylamine and a polar solvent such as N,N-dimethylformamide to form a reaction mixture which is quenched with aqueous acid to obtain an ester compound having the structural formula XIV

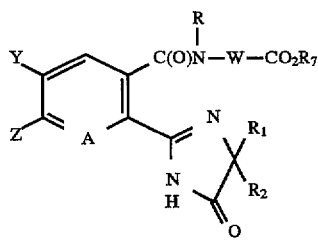   (XIV)

wherein Y, Z, W, $R_1$, $R_2$ and $R_7$ are as described hereinabove, saponifying the formula XIV ester compound with aqueous base and quenching the saponification reaction mixture with acid to form the desired formula I hapten. The reaction scheme is shown in Flow Diagram II.

FLOW DIAGRAM II

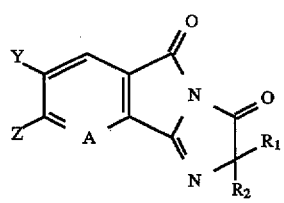

(XI)

1) $RN-W-CO_2R_7 + N(C_2H_5)_3$
   H
   (XIII)
2) aqueous acid

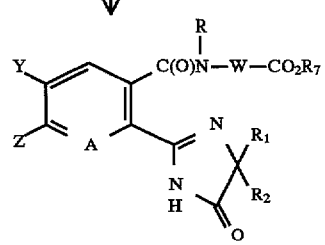

(XIV)

1) aqueous base
2) acid

-continued
FLOW DIAGRAM II

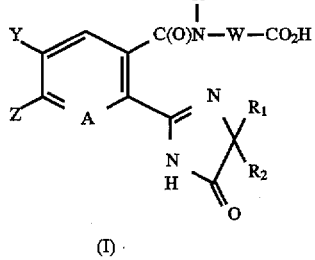

(I)

Formula II haptens may be prepared by reacting a compound having the structural formula XV

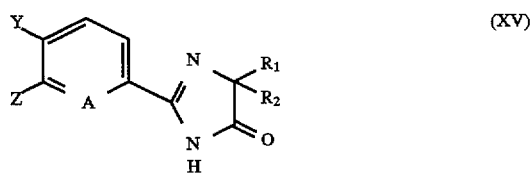   (XV)

wherein Y, Z, A, $R_1$ and $R_2$ are as described hereinabove with a metal hydride such as sodium hydride and a halo ester compound having the structural formula XVI $X_1W_1CO_2R_7$   (XVI)

wherein $W_1$ and $R_7$ are as described hereinabove; and $X_1$ is halogen to form a compound having the structural formula XVII

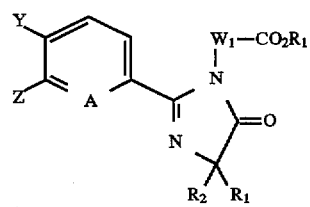   (XVII)

wherein Y, Z, $W_1$, $R_1$, $R_2$ and $R_7$ are as described hereinabove, saponifying the formula XVII compound with aqueous base and quenching the saponification reaction mixture with acid to obtain the desired formula II hapten. The reaction scheme is shown in Flow Diagram III.

FLOW DIAGRAM III

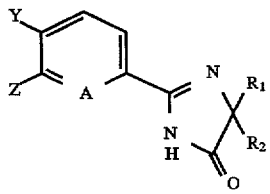

(XV)

1) NaH
2) $X_1W_1CO_2R_7$ (XVI)

-continued
FLOW DIAGRAM III

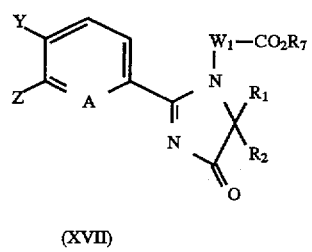

(XVII)

| 1) aqueous base
| 2) acid
↓

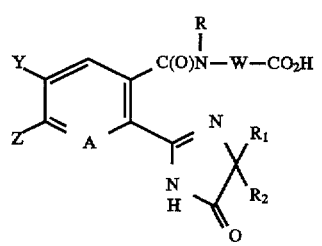

(II)

The antigens of the present invention may be prepared by reacting a hapten of the present invention with at least about one molar equivalent of 1-ethyl-3-(3-dimethylaminopropyl) carbodiimide hydrochloride to form an activated hapten and reacting the activated hapten with the amino groups of a protein to form the desired antigen. The above reaction scheme is shown in Flow Diagrams IV(a) and IV(b).

FLOW DIAGRAM IV(a)

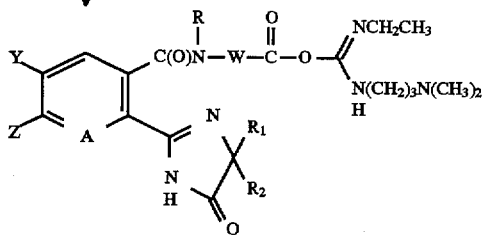

(I)

| $CH_3CH_2N=C=N(CH_2)_3N(CH_3)_2$
| .HCl
↓

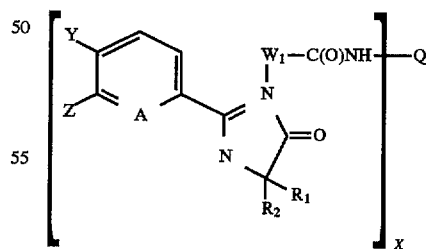

↓ Q—NH$_2$

FLOW DIAGRAM IV(a)

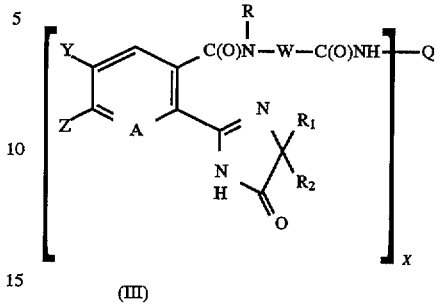

(III)

FLOW DIAGRAM IV(b)

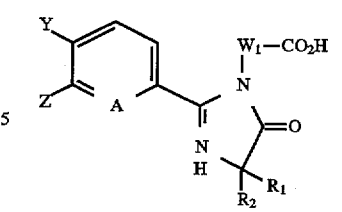

(II)

| $CH_3CH_2N=C=N(CH_2)_3N(CH_3)_2$
| .HCl
↓

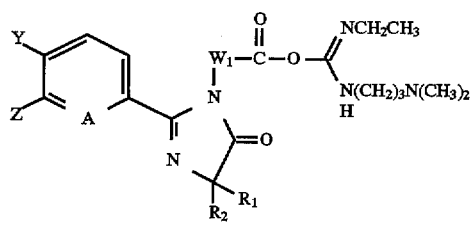

↓

↓ Q—NH$_2$

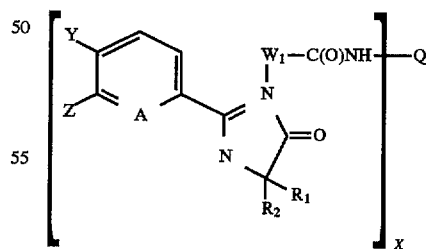

(IV)

Similarly, the enzyme conjugates of the present invention may be prepared as shown below in Flow Diagrams V(a) and v(b).

FLOW DIAGRAM V(a)

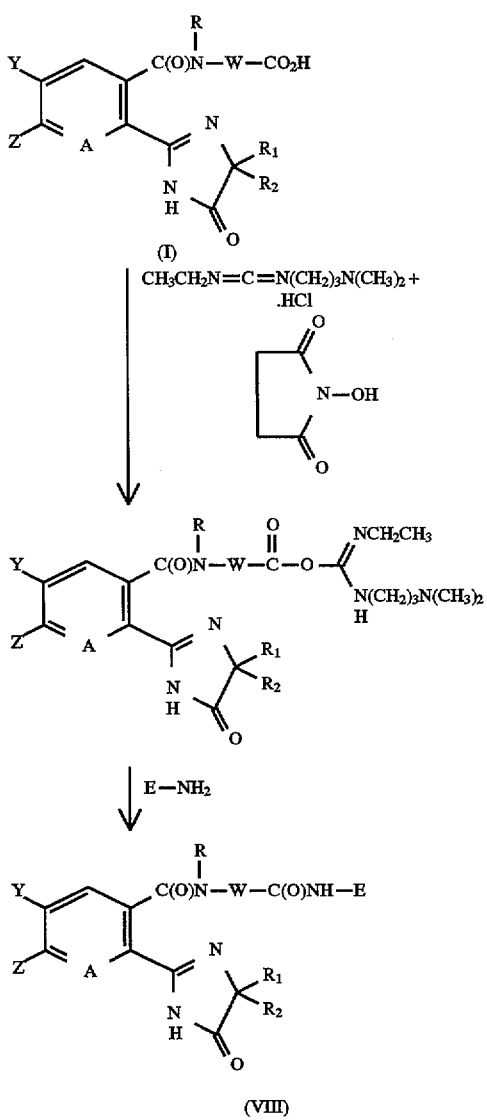

FLOW DIAGRAM IV(b)

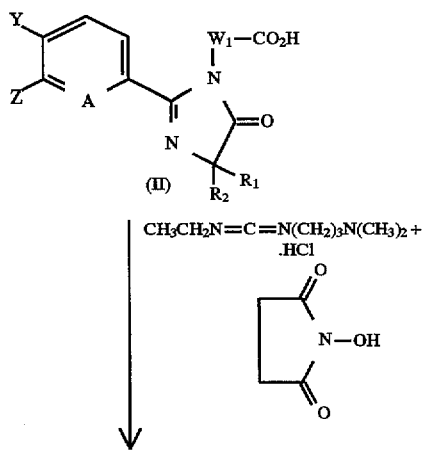

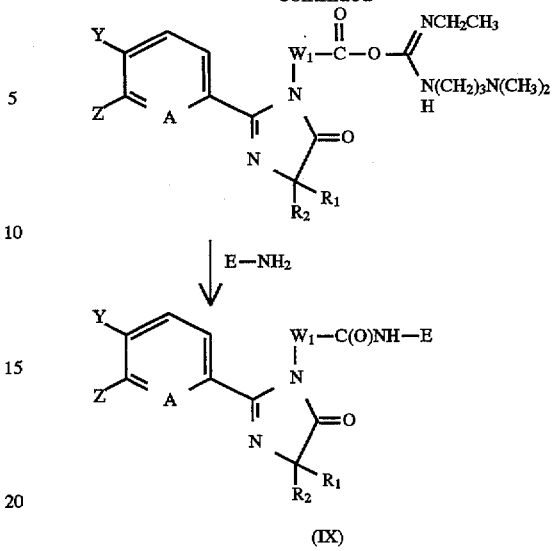

The antigens of the present invention are used to elicit imidazolinone specific antibody production in animals. Several weeks after an animal is immunized with one or more antigens, the serum is harvested and the polyclonal antibodies present in the serum may be used in indirect or direct immunoassays to determine the presence and quantity of imidazolinone compounds in soil, water or plant samples.

Advantageously, it has been found that certain hybridomas, prepared by fusing a spleen cell from an animal immunized with an antigen of the present invention with a myeloma cell, produce monoclonal antibodies which are specific for one imidazolinone compound among others. Heretofore, imidazolinone antibodies were not specific enough to allow for the accurate determination of the presence and quantity of an imidazolinone compound in the presence of one or more other imidazolinone compounds. The methods used to prepare the polyclonal antibodies, hybridomas and monoclonal antibodies of the present invention are described in the examples. Also described in the examples are the indirect and direct immunoassay methods which are used to determine the presence and quantity of an imidazolinone compound present in a sample.

The imidazolinone compounds are represented by structural formula XVIII

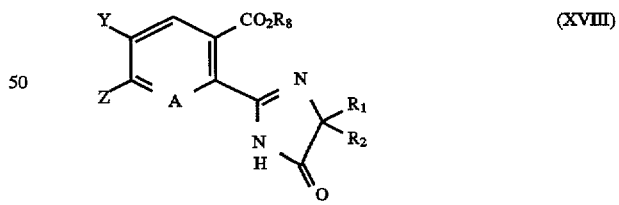

(XVIII)

wherein
Y, Z, A, $R_1$ and $R_2$ are as described hereinabove; and $R_8$ is hydrogen or $C_1$–$C_4$alkyl.

The polyclonal and monoclonal antibodies of this invention are especially useful in indirect and direct immunoassays to determine the presence and quantity of the following imidazolinone compounds:

5-ethyl-2-(4-isopropyl-4-methyl-5-oxo-2-imidazolin-2-yl) nicotinic acid (imazethapyr);

2-(4-isopropyl-4-methyl-5-oxo-2-imidazolin-2-yl)-3-quinolinecarboxylic acid (imazaquin);

mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate (imazamethabenz-methyl);

2-(4-isopropyl-4-methyl-5-oxo-2-imidazolin-2-yl)nicotinic acid (imazapyr); and 2-(4-isopropyl-4-methyl-5-oxo-2-imidazolin-2-yl)-5-methylnicotinic acid (imazamethapyr).

In order to facilitate a further understanding of the invention, the following examples are presented primarily for the purpose of illustrating more specific details thereof. The invention should not be deemed limited thereby except as defined in the claims.

EXAMPLE 1

Preparation of 4-[5-Ethyl-2-(4-isopropyl-4-methyl-5-oxo-2-imidazolin-2-yl)-N-methylnicotinamido]butyric acid

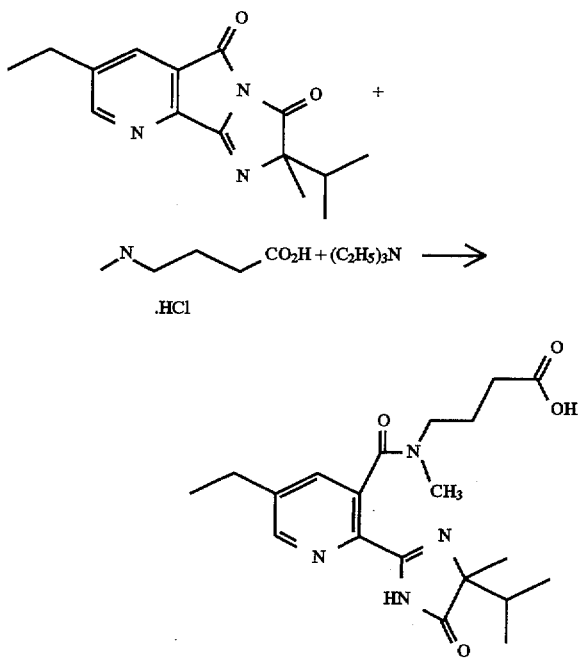

A stirred solution of 7-ethyl-2-isopropyl-2-methyl-5H-imidazo[1',2':1,2]pyrrolo[3,4-b]pyridine-3(2H),5-dione (5.47 g, 20.19 mmol) in anhydrous N,N-dimethylformamide is treated successively with 4-(methylamino)butyric acid hydrochloride (3.29 g, 21.2 mmol) and triethylamine (4.29 g, 42.39 mmol). The resulting mixture is stirred at room temperature under nitrogen for 2.5 hours. After this period, the reaction mixture is diluted with water, acidified with concentrated hydrochloric acid and extracted with ether. The organic extract is dried over magnesium sulfate, vacuum filtered through diatomaceous earth and concentrated in vacuo to give the title product as a white solid, mp 42°–49° C. (dec.).

EXAMPLE 2

Preparation of Methyl 6-[5-ethyl-2-(4-isopropyl-4-methyl-5-oxo-2-imidazolin-2-yl)nicotinamido]hexanoate

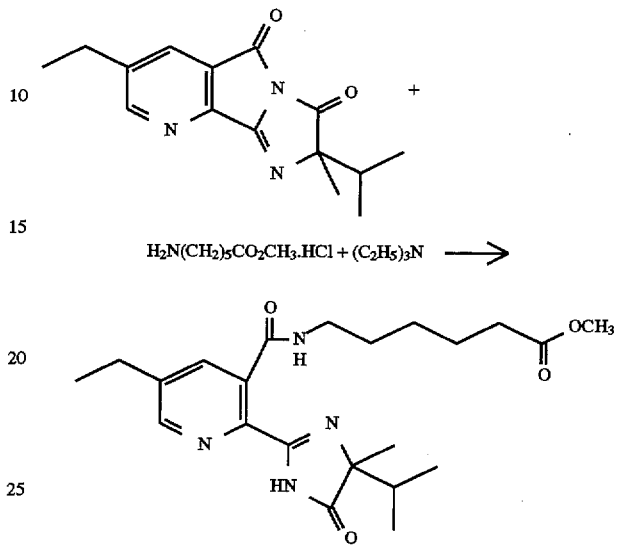

A stirred solution of 7-ethyl-2-isopropyl-2-methyl-5H-imidazo[1',2':1,2]pyrrolo[3,4-b]pyridine-3(2H),5-dione (7.25 g, 26.75 mmol) in anhydrous N,N-dimethylformamide is treated successively with methyl 6-aminocaproate hydrochloride (5.10 g, 28.1 mmol) and triethylamine (3.00 g, 29.6 mmol). The resulting mixture is stirred at room temperature under nitrogen for 20.5 hours. After this period, the reaction mixture is partitioned between water and ethyl acetate. The layers are separated, and the organic layer is washed with water, dried over magnesium sulfate and vacuum filtered through diatomaceous earth. The filtrate is concentrated in vacuo to obtain a white solid. The solid is triturated with 1:1 ether/petroleum ether to give the title product as a white solid (7.40 g, 69%, mp 101°–103° C.).

Using essentially the same procedure, but substituting methyl 4-aminobutyrate hydrochloride for 6-aminocaproate hydrochloride, methyl 4-[5-ethyl-2-(4-isopropyl-4-methyl-5-oxo-2-imidazolin-2-yl)nicotinamido]butyrate is obtained as a white solid, mp 132°–134° C.

EXAMPLE 3

Preparation of 6-[5-Ethyl-2-(4-isopropyl-4-methyl-5-oxo-2-imidazolin-2-yl)nicotinamido]hexanoic acid

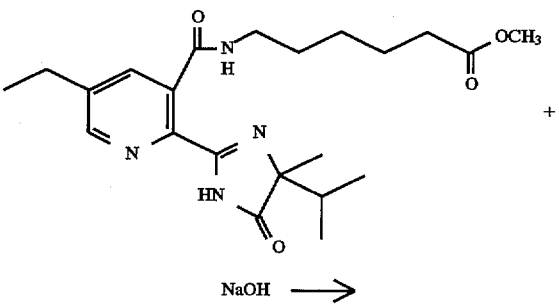

-continued

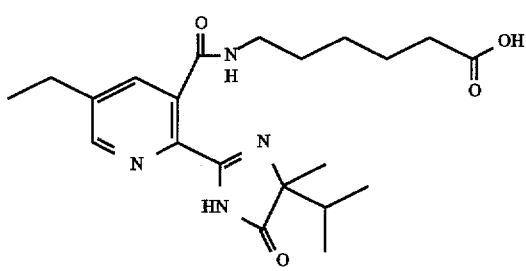

A stirred solution of methyl 6-[5-ethyl-2-(4-isopropyl-4-methyl-5-oxo-2-imidazolin-2-yl)nicotinamido]hexanoate (5.14 g, 12.35 mmol) in tetrahydrofuran is treated with 2N sodium hydroxide (15 mL). The resulting mixture is stirred at room temperature for 24 hours. After this period, the reaction mixture is concentrated in vacuo to obtain a residue. The residue is cooled with an ice bath and acidified with concentrated hydrochloric acid. The resulting precipitate is isolated by vacuum filtration and washed with water to give the title product as a white solid, mp 76°–81° C.

Using essentially the same procedure, but substituting methyl 4-[5-ethyl-2-(4-isopropyl-4-methyl-5-oxo-2-imidazolin-2-yl)nicotinamido]butyrate for 6-[5-ethyl-2-(4-isopropyl-4-methyl-5-oxo-2-imidazolin-2-yl)-nicotinamido]hexanoate, 4-[5-ethyl-2-(4-isopropyl-4-methyl-5-oxo-2-imidazolin-2-yl)nicotinamido]butyric acid is obtained as a solid, mp 165°–167° C.

EXAMPLE 4

Preparation of Ethyl 2-5-ethyl-2-pyridyl-4-isopropyl-4-methyl-5-oxo-2-imidazoline-1-crotonate, (E)-

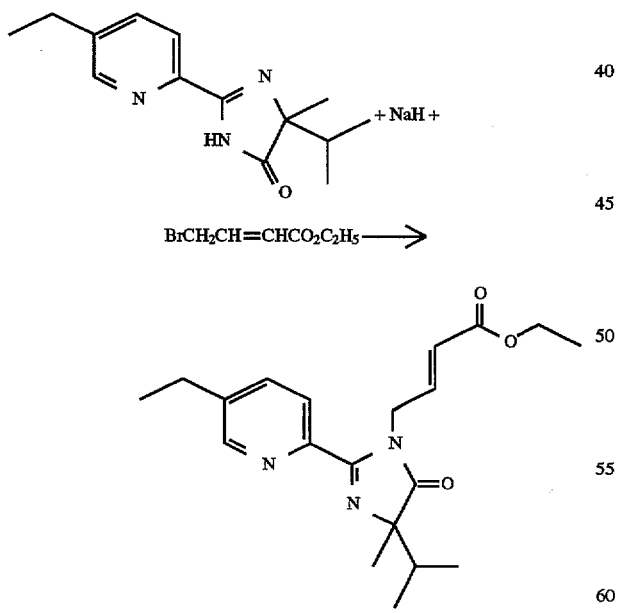

A stirred suspension of sodium hydride (1.6 g, 53 mmol, 80% oil dispersion) in dry tetrahydrofuran is treated with a solution of 2-(5-ethyl-2-pyridyl)-4-isopropyl-4-methyl-5-oxo-2-imidazoline (10.24 g, 41.80 mmol) in dry tetrahydrofuran dropwise via addition funnel. After addition is complete and effervescence subsides, ethyl 4-bromocrotonate (12.9 g, 50.1 mmol, 75% technical grade) is added to the reaction mixture at once. The resulting mixture is stirred at room temperature under nitrogen for 19 hours. After this period, the reaction mixture is partitioned between water and ether. The layers are separated, and the organic layer is dried over magnesium sulfate, decolorized with activated charcoal, vacuum filtered through diatomaceous earth, and concentrated in vacuo to obtain a dark brown oil. The oil is purified by flash chromatography (2:1 hexanes/ethyl acetate eluent) to give the title product as a pale orange oil (3.78 g, 25%).

EXAMPLE 5

Preparation of 2-5-ethyl-2-pyridyl-4-isopropyl-4-methyl-5-oxo-2-imidazoline-1-crotonic acid, (E)-

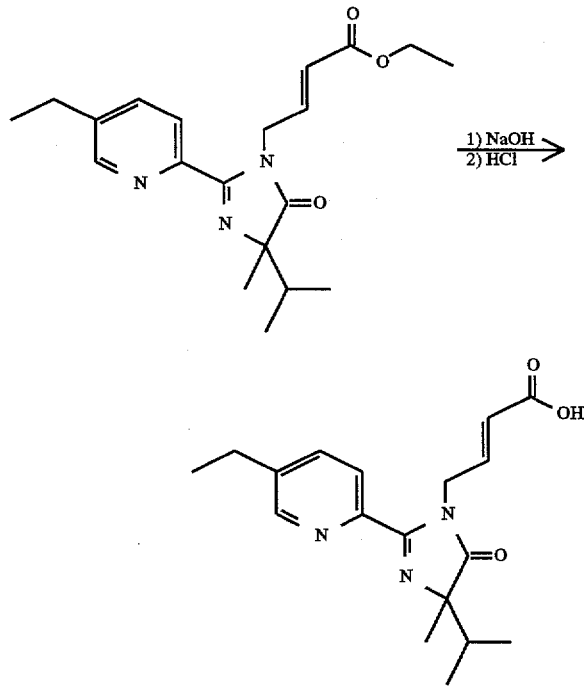

A stirred solution of ethyl 2-(5-ethyl-2-pyridyl)-4-isopropyl-4-methyl-5-oxo-2-imidazoline-1-crotonate, (E)- (1.16 g, 3.25 mmol) in 1:1 tetrahydrofuran/water is treated with sodium hydroxide (0.45 g, 11.3 mmol) at once. The resulting mixture is stirred at reflux for 1.5 hours, then at room temperature for 16.5 hours. After this period, the reaction mixture is diluted with water, and washed with ether. The aqueous layer is acidified with 1N hydrochloric acid (15 mL), and extracted with ether. The organic extract is dried over sodium sulfate, decolorized with charcoal and vacuum filtered through diatomaceous earth. The filtrate is concentrated in vacuo to give the title product as a yellow solid, mp 53°–58° C.

EXAMPLE 6

Preparation of Ethyl 2-(5-ethyl-2-pyridyl-4-isopropyl-4-methyl-5-oxo-2-imidazoline-1-acetate

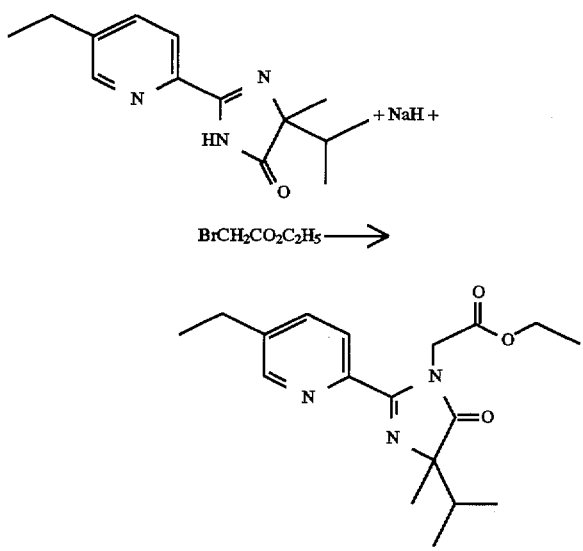

A stirred mixture of sodium hydride (0.45 g, 15 mmol, 80% oil dispersion) in anhydrous tetrahydrofuran is treated with a solution of 2-(5-ethyl-2-pyridyl)-4-isopropyl-4-methyl-5-oxo-2-imidazoline (3.30 g, 13.47 mmol) in anhydrous tetrahydrofuran dropwise over the course of 40 minutes. After addition is complete and the initial effervescence subsides, ethyl bromoacetate (2.30 g, 13.50 mmol) is added to the reaction mixture. After 24 hours stirring at room temperature under nitrogen, the reaction mixture is partitioned between water and ether. The layers are separated, and the organic layer is dried over magnesium sulfate, vacuum filtered through diatomaceous earth and concentrated in vacuo to obtain a residue. The residue is purified by flash chromatography (2:1 hexanes/ethyl acetate eluent) to give the title product as a pale yellow oil.

Using essentially the same procedure, but substituting ethyl 5-bromovalerate for ethyl bromoacetate, ethyl 2-(5-ethyl-2-pyridyl)-4-isopropyl-4-methyl-5-oxo-2-imidazoline-1-valerate is obtained as a gum.

EXAMPLE 7

Preparation of 2-(5-Ethyl-2-pyridyl-4-isopropyl-4-methyl-5-oxo-2-imidazoline-1-acetic acid

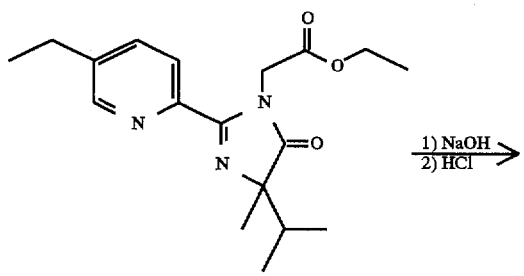

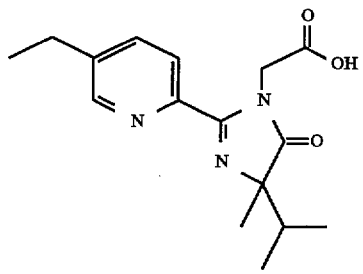

A stirred solution of ethyl 2-(5-ethyl-2-pyridyl)-4-isopropyl-4-methyl-5-oxo-2-imidazoline-1-acetate (2.12 g, 6.41 mmol) in tetrahydrofuran is treated with 2N sodium hydroxide (8 mL). The resulting mixture is stirred at room temperature for 16 hours. After this period, the reaction mixture is concentrated in vacuo to obtain a residue. The residue is acidified with concentrated hydrochloric acid and then extracted with ether. The organic extract is dried over magnesium sulfate, vacuum filtered through diatomaceous earth and concentrated in vacuo to give the title product as a white solid, mp 134°–136° C.

Using essentially the same procedure, but substituting ethyl 2-(5-ethyl-2-pyridyl)-4-isopropyl-4-methyl- 5-oxo-2-imidazoline-1-valerate for ethyl 2-(5-ethyl-2-pyridyl) -4-isopropyl-4-methyl-5-oxo-2-imidazoline-1-acetate, 2-(5-ethyl-2-pyridyl)-4-isopropyl-4-methyl-5-oxo-2-imidazoline-1-valeric acid is obtained as a gum.

EXAMPLE 8

Antigen preparation

The hapten prepared in Example 3, 6-[5-ethyl-2-(4-isopropyl-4-methyl-5-oxo-2-imidazolin-2-yl)nicotinamido] hexanoic acid (16.5 mg, 0.04 mmol), is dissolved in 100 µL of tetrahydrofuran and diluted to 0.5 mL with an alkaline aqueous buffer (pH 7.2–7.6). 1-Ethyl-3-(3-dimethylaminopropyl)carbodiimide hydrochloride (8.8 mg, 0.04 mmol) is added to the hapten solution to generate activated carboxyl groups on the hapten. The mixture containing the activated hapten is added to a solution of keyhole limpet hemocyanin (KLH, 10 mg, 22 nmol) in alkaline aqueous buffer (pH 7.2–7.6). The final molar ratio of hapten to total protein amino groups is greater than 100 to 1. The reaction mixture is stirred for 2 hours at room temperature and passed through molecular sieving columns to remove excess reagents. The antigen fraction is filtered through a 0.22µ filter and stored at 4° C. Flow Diagram VI illustrates the above reactions.

FLOW DIAGRAM VI

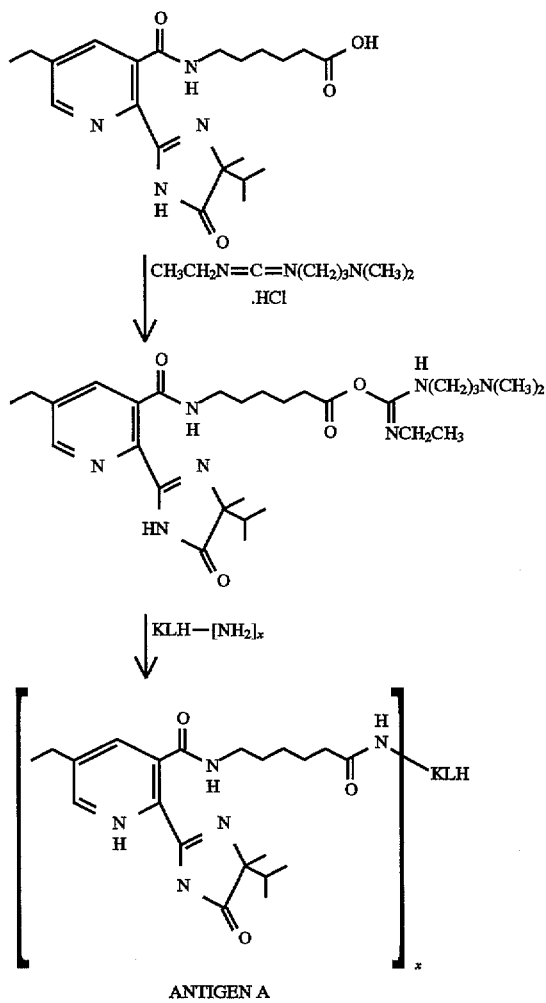

ANTIGEN A wherein

X is an integer of 1 to 40; and

KLH is keyhole limpet hemocyanin.

Using essentially the same procedure, the following antigens are prepared:

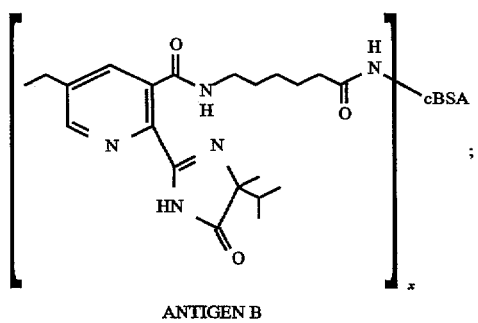

ANTIGEN B

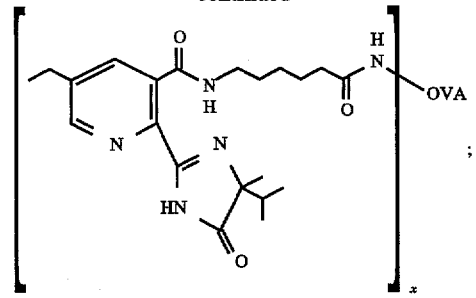

ANTIGEN C

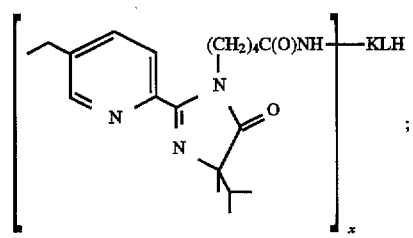

ANTIGEN D

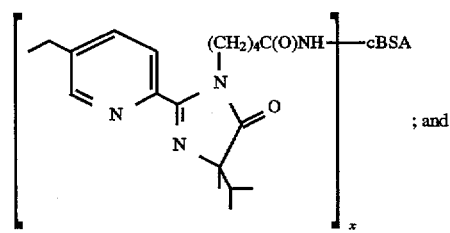

ANTIGEN E

; and

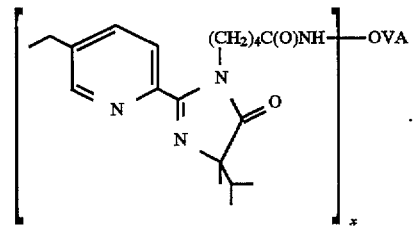

ANTIGEN F wherein

X is an integer from about 1 to 40;

cBSA is cationized bovine serum albumin;

OVA is ovalbumin; and

KLH is keyhole limpet hemocyanin.

EXAMPLE 9

Immunization of mice

Pairs of mice of the Swiss Webster and Biozzi strains are immunized with antigens A, B, D and E, prepared in Example 8. The initial doses consist of 50 µg of antigen in 0.1 mL of physiological saline and one mouse dose (about 50 µg) of Ribi adjuvant ("MPL+TDM Emulsion," Ribi Immunochem Research, Hamilton, Mont.). Booster doses are given 7 and 22 days after the first dose and consist of 25 µg of antigen in saline with Ribi adjuvant. Immunizations are subcutaneous, in 3 or 4 sites on the back of the mouse. Sera are taken on the twenty-ninth day after the first injection. Titers are determined by indirect enzyme immunoassay and then analyzed for ability to bind free imidazolinones in an indirect competition enzyme immunoassay as described below.

Enzyme immunoassays

An indirect enzyme immunoassay is used to screen for the production of anti-imidazolinone anti-bodies in the serum of the immunized mice and in cell fusion cultures. The method used is essentially the same as the method described by Voller, et al (Manual of Clinical Immunology, eds. N. Rose Friedman, H., pp. 506–512, 1976). For the indirect enzyme immunoassays, an antigen is adsorbed onto polystyrene flat bottom wells in 0.1M $Na_2CO_3$ buffer pH 9.6. Excess unbound material is washed away with buffer (PBS, containing 0.01M $NaH_2PO_4Na_2HPO_4$ pH 7.6 with 0.05% Tween®20 and 0.02% $NaN_3$). A 0.05% gelatin solution prepared in PBS is used to block the sites unoccupied by the antigen to prevent non-specific binding of reagents. Antibody from serum or culture are added into the wells for binding to the bound antigen. The wells are washed and the amount of bound anitbody is determined by adding alkaline phosphatase-conjugated goat anti-mouse IgG (Boehringer) to the wells followed by the addition of a p-nitrophenyl phosphate solution for color development. The color intensity is determined spectrophotometrically and is used to determine the titers.

In the indirect competition enzyme immunoassay, sera or cell fusion cultures which exhibit high titers are added to wells containing bound antigen in the presence of an imidazolinone solution. The bound antigen and imidazolinone compound compete for the antibody molecules. The wells are then washed and the color is developed as described above. In this assay, the color is inversely proportional to the amount of imidazolinone compound. In practice, standard curves are generated with known amounts of an imidazolinone compound and amounts present in test samples are calculated by interpolation.

EXAMPLE 10

Preparation of hybridomas

The best responding Swiss Webster mouse is "hyperimmunized" by intravenous injection of 50 μg of antigen in saline, 4 days prior to cell fusion which is about 60 days after the first immunization. The hybridomas are prepared by fusing spleen cells from the mouse with P3X63AG8.653 myeloma cells by electrofusion. The reagent buffers and cell culture media used are essentially the same as described by B. Forghani and A. E. Karu, Virology LabFAX, eds. DR Harper, pp. 187–214, Oxford: Bios Scientific Publishers Ltd., 1993. The electrofusion is performed as described by A. E. Karu et al, Journal of Agricultural and Food Chemistry, 42, pp. 301 . 309, 1994.

Four hundred hybridoma colonies are screened in 4 groups over a 12 day period. Eighty-four of the hybridoma colonies react with the antigens shown below.

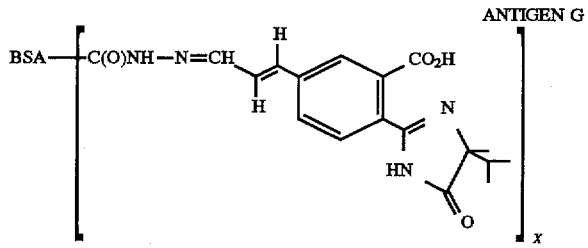

wherein

X is an integer from about 10 to 40.

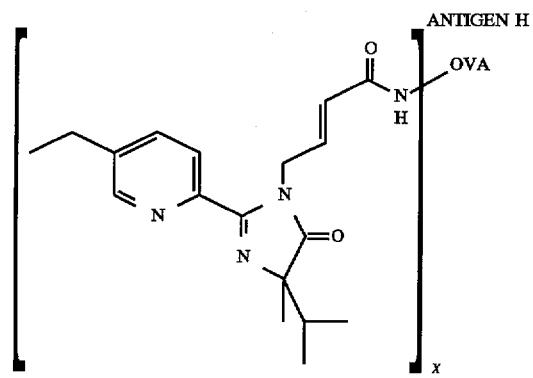

wherein

X is an integer from about 1 to 40.

Only one monoclonal antibody generated from one of the hybridoma colonies specifically binds antigen H and 83 monoclonal antibodies from culture supernatants react with antigen G. The cell lines are expanded to 24 well culture dishes. Seventeen of the 24 well cultures test positive in a second indirect enzyme immunoassay and 11 of these competitively bind imidazolinone compounds in competition enzyme immunoassays. Cultures that produce nonspecific, adventitious-binding antibodies are eliminated by enzyme immunoassay on plates coated with keyhole limpet hemocyanin. Table I lists all of the monoclonal antibodies (MAbs) that remain after the secondary screening.

TABLE I

| MAb |
| --- |
| 1A5.5 |
| 2C6.5 |
| 3A2.2 |
| 1D2.6 |
| 1B5.6 |
| 1B5.7 |
| 3A5.1 |
| 4A6 |

EXAMPLE 11

Specificities of the monoclonal antibodies in competition enzyme immunoassays

Indirect competition enzyme immunoassays for several imidazolinone compounds, using various monoclonal antibodies and antigens, are conducted according to the procedure described in Example 9. Table II summarizes the half-maximal dose responses. Antigens G and H are as described in Example 10 and Antigen I is shown below.

As can be seen from the data in Table II, monoclonal antibodies 1A5.5 and 1D2.6 bind imazethapyr with greater affinity when compared to the other imidazolinone compounds.

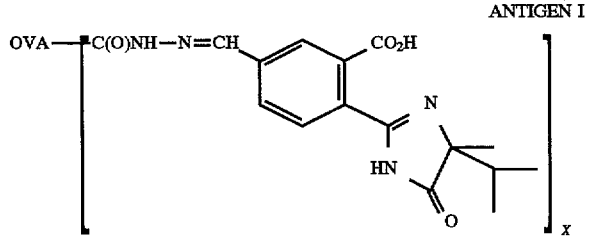

ANTIGEN I wherein

X is an integer from about 10 to 40.

lin which is previously adsorbed onto the polystyrene plate wells. The wells are washed with buffer (PBS, containing 0.01M $NaH_2PO_4$—$Na_2HPO_4$ pH 7.6 with 0.05% Tween®20 and 0.02% $NAN_3$) and blocked with a 0.05% gelatin solution prepared in PBS. Standard solutions having concentrations of imazapyr from 0 to 5,000 ng/mL are added to the blocked wells followed by the addition of the aforementioned enzyme conjugate.

After several minutes, the wells are washed and the color is developed by adding BRL alkaline phosphatase substrate amplification kit (commercially available from GIBCO BRL Life Technologies Inc., Gettysburg, Md.). After several

TABLE II

Competitive Binding of Imidazolinones in Indirect Enzyme Immunoassays
Values are I$_{50}$(half-maximal inhibition) in ppb (ng/mL)

| Imidazolinone Compound | Monoclonal Antibody Coating Antigen | 1A5.5 H | 1D2.6 I | G | 2C6.5 I | G | 3A2.2 I | G | 3A5.1 I | G |
|---|---|---|---|---|---|---|---|---|---|---|
| Imazethapyr | | 60 | 20 | >10,000 | 15 | 13 | 21 | 34 | 220 | >1,000 |
| Imazapyr | | 500 | >1,000 | >10,000 | NC | NC | 331 | 290 | >5,000 | NC |
| Imazaquin | | >1,000 | 2,000 | >10,000 | NC | NC | 3 | 5 | 800 | NC |
| Imazamethabenz-methyl | | 500 | 105 | >10,000 | NC | NC | 356 | 322 | 90 | 400 |
| Imazamethapyr | | 100 | 250 | >10,000 | 204 | 171 | 27 | 31 | 340 | >1,000 |

NC = no competition

EXAMPLE 12

Preparation of an enzyme conjugate

A solution of 1-ethyl-3-(3-dimethylaminopropyl) carbodiimide (11.7 mg, 0.06 mmol) and N-hydroxysuccinimide (13.1 mg, 0.06 mmol) in 1:1 N,N-dimethylformamide/water is added to a solution of 6-[5-ethyl-2-(4-isopropyl-4-methyl-5-oxo-2-imidazolin-2-yl)nicotin-amide]hexanoic acid (24.7 mg, 0.06 mmol) in N,N-dimethylformamide. After stirring for 3.5 hours, the reaction mixture is slowly added to an alkaline phosphatase solution in 0.05M sodium borate buffer pH 7.5 with 0.9% NaCl. The resultant mixture is stirred at 4° C. for 18 hours and passed through an agarose column to give an enzyme conjugate having the structural formula shown below.

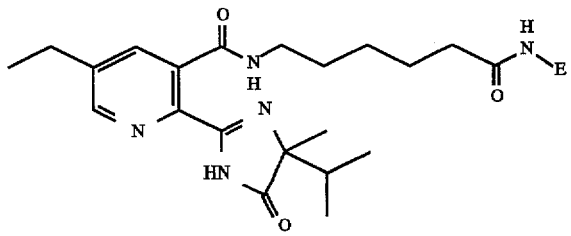

wherein E is alkaline phosphatase.

EXAMPLE 13

Direct competition enzyme immunoassay

The monoclonal antibody 3A2.2 prepared in Example 10 and the enzyme conjugate prepared in Example 12 are used to establish a direct competition enzyme immunoassay method for the determination of the concentration of imazapyr in samples. A constant amount of the monoclonal antibody 3A2.2 is adsorbed onto polystyrene plate wells through an affinity purified goat anti-mouse immunoglobuminutes, readings are taken for each well at 490 nm using a microwell reader.

A standard curve plot having the log of imazapyr concentration on the x-axis and the optical density reading at 490 nm (OD 490) on the Y-axis is used to determine unknown concentrations of imazapyr present in soil, water or plant samples from their OD 490 values.

The OD 490 readings for 6 imazapyr standard solutions and a solvent blank are obtained from a direct enzyme immunoassay experiment run in triplicate. The means and standard deviations are calculated and are summarized in Table III. The standard curve obtained by plotting the mean OD 490 reading versus the logarithm of the standard imazapyr concentration is used to determine unknown imazapyr concentrations from about 0.5 ng/mL to 500 ng/mL.

TABLE III

| Imazapyr Concentration (ng/mL) | OD 490 Reading | Standard Deviation |
|---|---|---|
| 0.00 | 2.616 | 0.125 |
| 0.05 | 2.671 | 0.096 |
| 0.50 | 2.507 | 0.094 |
| 5.0 | 1.893 | 0.078 |
| 50 | 0.801 | 0.033 |
| 500 | 0.474 | 0.012 |
| 5,000 | 0.446 | 0.001 |

What is claimed is:

1. An imidazolinone hapten having the structural formula

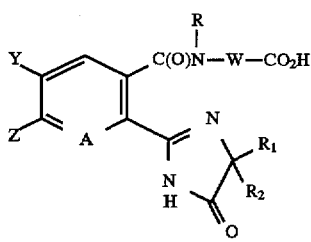

wherein

R is hydrogen or $C_1$–$C_4$alkyl;

$R_1$ is $C_1$–$C_4$alkyl;

$R_2$ is $C_1$–$C_4$alkyl or $C_3$–$C_6$cycloalkyl; and when $R_1$ and $R_2$ are taken together with the carbon atom to which they are attached they may represent $C_3$–$C_6$cycloalkyl optionally substituted with methyl;

Y and Z are each independently hydrogen, halogen, $C_1$–$C_6$-alkyl, $C_1$–$C_4$alkoxyalkyl, $C_1$–$C_4$hydroxyalkyl, $C_1$–$C_4$alkoxy, $C_1$–$C_4$alkylthio, phenoxy, $C_1$–$C_4$haloalkyl, nitro, cyano, $C_1$–$C_4$alkylamino, di($C_1$–$C_4$alkyl) amino, $C_1$–$C_4$alkylsulfonyl or phenyl optionally substituted with one $C_1$–$C_4$alkyl group, $C_1$–$C_4$alkoxy group or halogen atom;

A is N or CH;

W is $C_3$–$C_{12}$alkylene optionally substituted with one or two $C_1$–$C_3$alkyl groups, $C_1$–$C_3$alkoxy groups, oxo groups or halogen atoms, and optionally interrupted by one oxygen or sulfur atom, $C_3$–$C_{12}$alkenylene optionally substituted with one or two $C_1$–$C_3$alkyl groups, $C_1$–$C_3$alkoxy groups, oxo groups or halogen atoms, and optionally interrupted by one oxygen or sulfur atom, or $C_3$–$C_{12}$alkynylene optionally substituted with one or two $C_1$–$C_3$alkyl groups, $C_1$–$C_3$alkoxy groups, oxo groups or halogen atoms, and optionally interrupted by one oxygen or sulfur atom.

2. The imidazolinone hapten according to claim 1 wherein

R is hydrogen or methyl;

$R_1$ is methyl;

$R_2$ is isopropyl;

Y is hydrogen, $C_1$–$C_4$alkyl or $C_1$–$C_4$alkoxyalkyl;

Z is hydrogen;

A is N or CH;

W is $C_3$–$C_{12}$alkylene or $C_3$–$C_{12}$alkenylene.

3. The imidazolinone hapten according to claim 2 wherein

R is hydrogen or methyl;

$R_1$ is methyl;

$R_2$ is isopropyl;

Y is hydrogen, methyl, ethyl or methoxymethyl;

Z is hydrogen;

A is N;

W is $C_3$–$C_6$alkylene or $C_3$–$C_6$alkenylene.

4. The imidazolinone hapten according to claim 3,

6-[5-ethyl-2-(4-isopropyl-4-methyl-5-oxo-2-imidazolin-2-yl)nicotinamido]hexanoic acid.

5. The imidazolinone hapten according to claim 3,

4-[5-ethyl-2-(4-isopropyl-4-methyl-5-oxo-2-imidazolin-2-yl)nicotinamido]butyric acid.

6. The imidazolinone hapten according to claim 3,

4-[5-ethyl-2-(4-isopropyl-4-methyl-5-oxo-2-imidazolin-2-yl)-N-methylnicotinamido]butyric acid.

7. A compound having the structural formula

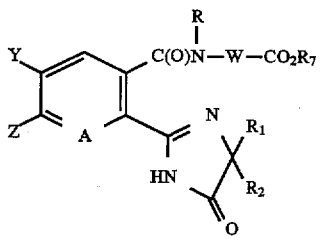

wherein

R, $R_1$, $R_2$, Y, Z, A, W are as described in claim 1; and $R_7$ is $C_1$–$C_4$alkyl.

8. The compound according to claim 7, wherein

R is hydrogen or methyl;

$R_1$ is methyl;

$R_2$ is isopropyl;

Y is hydrogen, $C_1$–$C_4$alkyl or $C_1$–$C_4$alkoxyalkyl;

Z is hydrogen;

A is N or CH;

W is $C_3$–$C_{12}$alkylene or $C_3$–$C_{12}$alkenylene.

9. The compound according to claim 8 wherein

R is hydrogen or methyl;

$R_1$ is methyl;

$R_2$ is isopropyl;

Y is hydrogen, methyl, ethyl or methoxymethyl;

Z is hydrogen;

A is N;

W is $C_3$–$C_6$alkylene or $C_3$–$C_6$alkenylene; and $R_7$ is methyl or ethyl.

10. The compound according to claim 9, methyl 6-[5-ethyl-2-(4-isopropyl-4-methyl-5-oxo-2-imidazolin-2-yl)nicotinamido]hexanoate.

11. The compound according to claim 9, methyl 4-[5-ethyl-2-(4-isopropyl-4-methyl-5-oxo-2-imidazolin-2-yl)nicotinamido]butyrate.

* * * * *